United States Patent
Auvray et al.

(10) Patent No.: US 9,583,075 B2
(45) Date of Patent: Feb. 28, 2017

(54) DEVICE POSITION DEPENDANT OVERLAY FOR ROADMAPPING

(71) Applicant: KONINKLIJKE PHILIPS N.V., Eindhoven (NL)

(72) Inventors: Vincent Maurice Andre Auvray, Meudon (FR); Raoul Florent, Ville D'Avray (FR)

(73) Assignee: KONINKLIJKE PHILIPS N.V., Eindhoven (NL)

(*) Notice: Subject to any disclaimer, the term of this patent is extended or adjusted under 35 U.S.C. 154(b) by 5 days.

(21) Appl. No.: 14/415,057

(22) PCT Filed: Jul. 24, 2013

(86) PCT No.: PCT/IB2013/056064
§ 371 (c)(1),
(2) Date: Jan. 15, 2015

(87) PCT Pub. No.: WO2014/020495
PCT Pub. Date: Feb. 6, 2014

(65) Prior Publication Data
US 2015/0179148 A1   Jun. 25, 2015

(30) Foreign Application Priority Data

Aug. 3, 2012   (EP) .................................... 12305961

(51) Int. Cl.
*G09G 5/00* (2006.01)
*A61B 6/00* (2006.01)
(Continued)

(52) U.S. Cl.
CPC ............... *G09G 5/377* (2013.01); *A61B 6/12* (2013.01); *A61B 6/487* (2013.01); *A61B 6/504* (2013.01);
(Continued)

(58) Field of Classification Search
None
See application file for complete search history.

(56) References Cited

U.S. PATENT DOCUMENTS 6,341,231 B1    1/2002  Ferre
7,454,043 B2*  11/2008  Eck ........................ A61B 6/481
                                                        378/114
(Continued)

FOREIGN PATENT DOCUMENTS

WO         2012011036 A1    1/2012

OTHER PUBLICATIONS

Bredno et al, "Algorithmic Solutions for Live Device-To-Vessel Match", Proceedings of SPIE, vol. 5370, Medical Imaging 2004, pp. 1486-1497.
(Continued)

*Primary Examiner* — Ashish K Thomas

(57) ABSTRACT

An image processor (IP) and an image processing method to support cardio- or neuro-interventions. An imager (100) acquires a series of fluoroscopic images (F) while an interventional tool progresses through a region of interest (ROI) such as a cardiac vasculature. Image processor (IP) operates to select from a plurality of stored angiograms (A) previously acquired of the region of interest a contextual one from which a contextual roadmap (RM) can be extracted. The contextual roadmap is selected to fit to both, a current cardiac phase and the current position of the device (GW). The selected contextual angiogram and its contextual roadmap is capable of showing the outlines of the vasculature (ROI) at the current device position at high contrast.

17 Claims, 5 Drawing Sheets

(51) Int. Cl.
*G09G 5/377* (2006.01)
*A61B 6/12* (2006.01)
*G09G 5/02* (2006.01)

(52) U.S. Cl.
CPC .......... *A61B 6/5235* (2013.01); *A61B 6/5288* (2013.01); *G09G 5/026* (2013.01); *A61B 6/463* (2013.01); *A61B 6/481* (2013.01); *G09G 2340/12* (2013.01)

(56) References Cited

U.S. PATENT DOCUMENTS

| 8,554,308 | B2 | 10/2013 | Florent et al. | |
|---|---|---|---|---|
| 2004/0152974 | A1 | 8/2004 | Solomon | |
| 2005/0080327 | A1* | 4/2005 | Jenkins | A61B 6/481 600/407 |
| 2005/0207538 | A1* | 9/2005 | Mollus | A61B 6/541 378/132 |
| 2006/0257006 | A1* | 11/2006 | Bredno | A61B 6/12 382/128 |
| 2007/0055142 | A1 | 3/2007 | Webler | |
| 2007/0276216 | A1 | 11/2007 | Beyar | |
| 2010/0049034 | A1* | 2/2010 | Eck | A61B 6/12 600/424 |
| 2010/0049038 | A1* | 2/2010 | Florent | A61B 6/12 600/425 |
| 2010/0145193 | A1 | 6/2010 | Florent | |

OTHER PUBLICATIONS

Ruijters, D. et al "How to perform multi-modality 3D roadmapping in neurovascular procedures", European Society of Radiology, 2012.

Ruijters, D. et al, "3D Multimodality Roadmapping in Neuroangiography", Proceedings of SPIE—vol. 6509, Medical Imaging 2007.

INNOVA IGS 530 Interventional X-ray for Cardiology—Interventional Image Guided Systems, GE Healthcare, 2012.

Toshiba's New Volume Navigation 3D Roadmap Facilitates More Accurate Visualization During Complex Interventions, Business Wire 2010.

* cited by examiner

DEVICE POSITION DEPENDANT OVERLAY FOR ROADMAPPING

CROSS-REFERENCE TO PRIOR APPLICATIONS

This application is the U.S. National Phase application under 35 U.S.C. §371 of International Application Serial No. PCT/IB2013/056064, filed on Jul. 24, 2013, which claims the benefit of European Application Serial No. EP12305961.0, filed on Aug. 3, 2012. These applications are hereby incorporated by reference herein.

FIELD OF THE INVENTION

The present invention relates to an image processing apparatus, to an image processing method, to an image processing system, to a computer program element, and to a computer readable medium.

BACKGROUND OF THE INVENTION

Cardiac and neurological interventions are frequently supported by fluoroscopic imaging devices whilst a catheter is introduced into a patient's body by medical personnel. The device is progressed through a suitable feeder artery to a diseased or lesioned site.

Progression of the device is monitored by the radiologist on a screen. On said screen the fluoroscopic images are displayed which are acquired by an x-ray projection imager throughout the intervention. In a cardio context, it is the coronary vessels that are of interest where the lesion, for example a stenosis, is located. The vessels themselves are normally barely, if at all, visible in the fluoroscopic images because of the vessel's low radiation opacity. To still provide the radiologist with a navigational aid, road mapping techniques are used. A road map is a graphic that represents in projection view the outlines of an anatomic structure such as the vessel through which the catheter is made to progress. The road map is usually shown alongside the current fluoro to provide the desired navigational clue. A single road map in general does not cover the whole region of the coronaries through which the catheter travels. According to past solutions, a number of localized road maps have been stitched together into a composite road map to thereby provide the visual navigation aid.

US 2010/049038 describes a cardiac roadmapping procedure.

SUMMARY OF THE INVENTION

There may therefore be a need for an alternative apparatus to support medical personnel during interventional procedures.

The object of the present invention is solved by the subject matter of the independent claims where further embodiments ate incorporated in the dependent claims. It is understood that the following aspect of the invention equally apply to the image processing method, the image processing system, to the computer program element and to the computer readable medium.

According to a first aspect of the invention there is provided an image processing apparatus comprising;

an input port for receiving a projection image of a device acquired whilst said device resides at a position relative to an object. The object is capable of transitioning between at least a first and a second object state and said device repositionable;

an object state determiner configured to determine a current state of the object;

a device localizer configured to use image information in the received projection image to determine the position of the device;

an object image selector configured to select from of a plurality of stored object images a contextual object image i) whose group corresponds to the determined object state and ii) whose image information is indicative of the determined device position. The plurality of stored object images is grouped according to the first object state and the second object state, at least one group comprising more than one of the object images; and a graphics display generator configured to generate for display on a screen a combined image including a part of the selected contextual object image and the received device projection image.

According to one embodiment, the apparatus may be used in a cardio-setting for vessel roadmapping in interventional fluoroscopy. In this embodiment the device may be a medical intervention tool such as a guidewire guiding a catheter and the object is a patient's cardiac vasculature. The states of the vasculature are periodic position changes of the vasculature caused by the cardiac activity. The device projection images are fluoroscopic images acquired during the intervention and the object projection images are a grouped plurality of pre-recorded angiograms of the cardiac vasculature. The part of the contextual angiogram can then be extracted as a roadmap and can be combined with a current fluoroscopic image to form the combined image. The combined image can then be displayed on the screen to so provide to the clinician a visual aid for safely navigating the device through the vasculature during the intervention. The angiograms have been recorded over a number of cardiac cycles and the grouping is according to the respective cardiac phases with, according to one embodiment, each group comprising a plurality of angiograms recorded at the same cardiac phase and recorded when different parts of the vasculature was perfused ("filled") at different levels owing to the flow through the vasculature of angiographic contrast agent. In other words, a part of the vasculature's footprint as recorded in the angiograms from the same group would in general show in different shadings of grey for different ones of the angiograms when viewed on screen with an appropriate grey value mapping.

Unlike in previous systems, there is no fixed vascular roadmap for specific time instant nor is there the need to form ("stitch") for display one composite vascular roadmap from several time instants. In contrast, the proposed apparatus tailors and adapts its selection of the angiograms to the instant stream of fluoroscopic images. The apparatus uses the device position in the fluoro and the current cardiac phase to search during run-time of the fluoroscopic image stream acquisition for the contextual angiogram in a "stock pile" of angios stored in the group corresponding to the current cardiac phase. The selection is two-phase in that first the group, that is, the object's state is determined, and then in the second phase the angio is selected from said group.

According to one embodiment, the graphics display generator is configured to generate a new combined image when a new object state is determined by object state determiner. In other words, the combined image is dynamically updated and recomputed upon detection of a new object state. The search or selection operation for a new contextual image is refocused to a new group and upon selection of the updated contextual angiogram a new contextual roadmap extractable from same is displayed in a new combined image. In a similar manner the new selection is also triggered upon detection of a new device position. In short, the selection of the current contextual angiogram follows both, cardiac phase and device position.

According to one embodiment, if the group of the contextual image is determined to be the or a group having respectively the at least two object images or at least two object images, the object image selector is configured to use an image neighborhood around the device position in the device image to establish corresponding image neighborhoods in the at least two object images in the group of the matched object image. The selector is configured to use a scoring scheme to assign a score to each of the at least two object images, said score based on pixel values in the respective established image neighborhoods, wherein the contextual object image is the selected one of the at least two object images having a higher score than the at least one other object image. According to one embodiment, the pixel information is the contrast in said image neighborhood of the respective angiogram (or a filtered version thereof) in the group under consideration. In one embodiment, a ridge filter or other directional filter is used prior to comparing contrast in the respective neighborhoods around the current device position. Such filters respond to elongate image structures but it is understood that other filters may be used when other footprint shapes are expected. The device position may be taken as the position the device's tip in the case of a guidewire but other prominent and relevant portions of the device that determine the navigation path may equally be used to define said image neighborhood of the respective angiogram. Other embodiments included measuring contrast by computing root-means-square (RMS) of pixel intensities in the respective angiogram neighborhoods. In other words, the contextual image is spatially contextual in that it not only is capable of showing the vessel at the current device position but is capable of so showing said position at a high contrast compared to the remaining angiograms in said group. Put differently, the apparatus returns the contextual angiogram as one that i) is synchronized with the current cardiac phase, ii) is capable of showing the vasculature at the determined device position and iii) was acquired at a time when the contrast agent concentration or perfusion in the vasculature at the determined device position was higher than for all or the majority of angiograms acquired at the same cardiac phase.

According to one embodiment, the determination operation of determiner includes a matching operation to match the received device image to a matching object image among said plurality of stored object images and to return the state corresponding to said matching object image's group as the determined object state. According to one embodiment the matching is by filtering of the object's footprint in the object image and then by aligning the filtered object footprint with a filtered device footprint in the device image. The object footprint is then shifted so as to intersect the device footprint and to make said intersecting portion as large as possible for any pair of angiogram and the current device image. The angiogram whose shifted footprint defines the overall largest overlap or intersection area in the device footprint is then determined the matching angiogram and its group is then determined the current object state. For the cardio setting a directional filtering is used because elongate footprints are expected. In other setting other filters may be used that respond to the expected footprints shapes with may be round or ellipse shaped in other settings.

In some cases it may happen that the criteria to establish whether an angiogram is contextual or not are ambiguous resulting in a plurality of contextual images each satisfying the applicable criteria. According to one embodiment, to resolve this ambiguity and to output one single angiogram as contextual at any given instance, image selector operates to return the contextual image as the one having an acquisition time most proximate in time to a previously selected contextual image. Flickering can thereby be avoided or kept low when changing over from one roadmap to another. The time proximity to the previous contextual image is used in conjunction with above mentioned scoring. In one embodiment, both scorings are used so that a high contrast angiogram can still be determined as contextual although it is not the most proximate one and, inversely, from two angiograms whose local contrast scores are close, the most proximate one will be returned as the contextual angio.

According to one embodiment, the contextual roadmap extractable from the selected contextual angiogram is extracted upon selection. According to an alternative embodiment, roadmaps are extracted in a previous preparatory step from each of the angios and are then stored in association with their respective angiogram. Once an angiogram has been determined contextual relative to the cardiac phase and device position, the associated roadmap can then be retrieved as the contextual roadmap.

It is understood that in the above, reference to the cardio setting is an exemplary embodiment only. Other settings such as neurology are equally envisaged as application of the apparatus as proposed herein. In particular references to angiograms, fluoroscopic images, cardiac phase and cardiac vasculature and catheter/guidewire are for the sake of illustration of exemplary embodiments only. In particular, the object may be any organic or non-organic entity that is capable of changing among or assuming a plurality of states. State may refer to any one of different spatial or non-spatial configurations the object is capable of assuming so long as said states are recordable or can be evidenced in the object images. In particular, "object state" may refer to the patient's breathing cycle because the motion of the chest during breathing likewise affects the position of certain parts of the human (or animal) vasculature.

DEFINITION

By "Footprint" in an image as used herein is meant the image portion in a projection image that corresponds to the projection of a body (anatomic structure or medical device) onto the image plane of said image.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
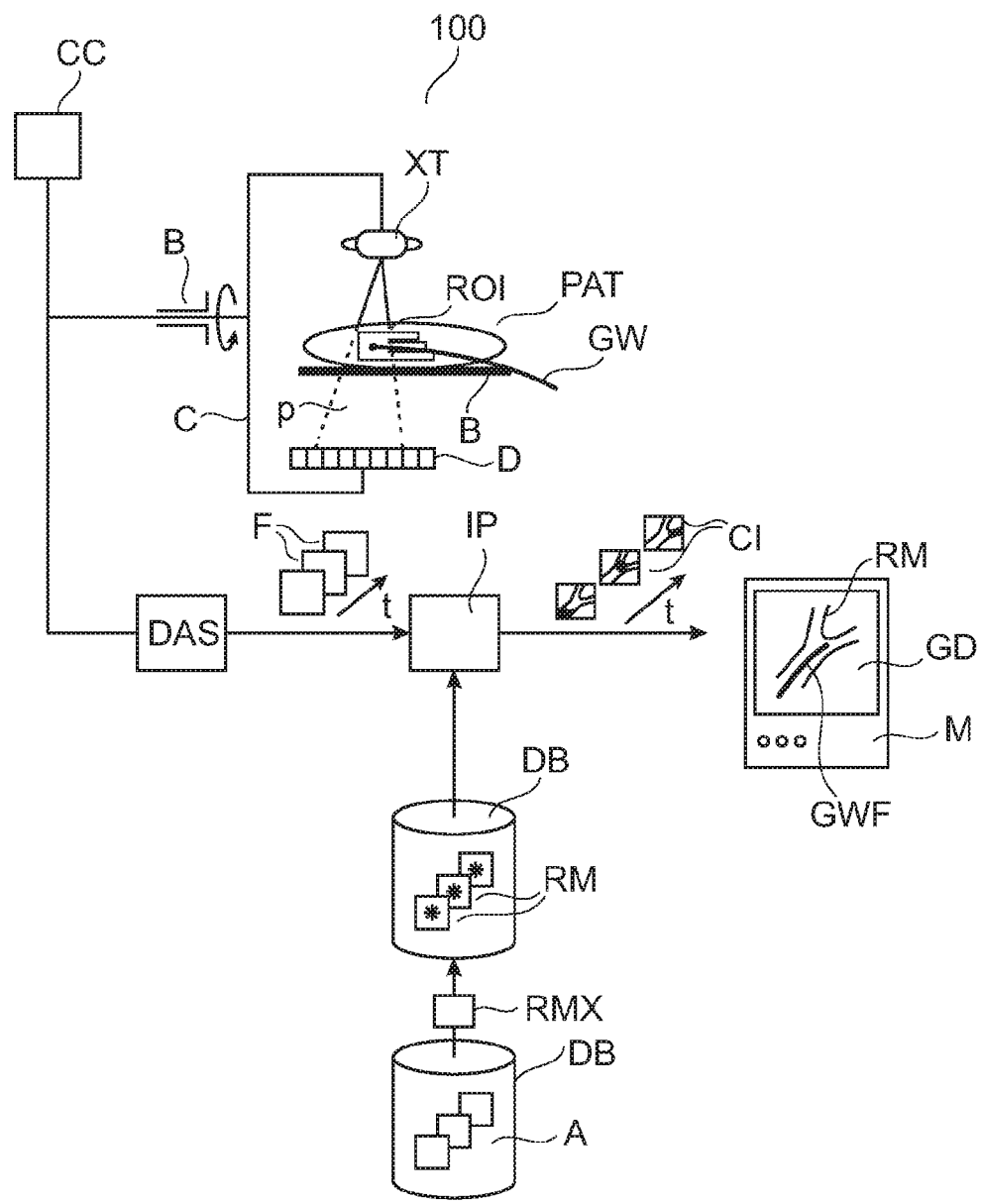
FIG. 1 shows an image processing arrangement including an imager and an image processor for supporting an intervention.

With reference to FIG. 1, the basic components of a fluoroscopic imaging arrangement are shown that can be used among others in interventional procedures.

A patient PAT may suffer from a stenosis or other lesion in his or her coronary vasculature ROI. During the interventional procedure, medical personnel introduces a guide wire GW into the femoral artery of patient PAT and then guides a catheter to the diseased portion in the patient's coronary vasculature ROI where the stenosis is located. As Guidewire GW progresses through patient's P cardiac vasculature, a series of sequential fluoroscopic images F are acquired by an x-ray imager 100.

During the intervention, patient PAT is deposed on a bed B between the imager 100's x-ray tube XT and detector D. X-ray tube XT and detector D are attached to rigid frame C rotatably mounted on a bearing B. The fluoroscopic image operation is controlled from a computer console CC. The interventional radiologist can control via said console CC image acquisition and can "shoot" each of the individual fluoroscopic frames (fluoros) by actuating a joy stick or a pedal. According to one embodiment, imager 100 is of the C-arm type.

During image acquisition an x-ray p emanates from x-ray tube XT, passes through the vasculature ROI, experiences attenuation by interaction with matter therein, and the so attenuated beam p then strikes detector D's surface at a one of plurality of detector cells making up detector D. Each cell that is struck by a beam responds by issuing a corresponding electric signal. The collection of said signals is then translated into a respective digital value representative of said attenuation. The density of the material making up the vasculature ROI determines the level of attenuation with high density material causing higher attenuation than less denser materials. The so registered digital values for each x-ray p are then consolidated into an array of digital values forming a fluoro for a given acquisition time and projection direction. In other words each fluoro is a digital image of a projection view along a projection direction and said direction is determined by the rotation of the C-arm at the given acquisition time or instant. The series of fluoros F are then digitally processed by data acquisition unit DAS and are then forwarded to an image processor IP whose purpose and operation will be explained in more detail below.

In the fluoroscopic image F it is in general only high attenuating objects whose footprint is discernible. More particularly, it is only the guidewire GW made of a high opacity material that is visible as an, in general, elongated footprint GWF in each fluoro. As the stream of fluoroscopic images F are acquired at a frame rate of about 30 images per second the progression of the guidewire GW through the patient PAT's body can be monitored.

The guidewire GW is used to guide for example a balloon catheter to the lesioned site.

It is the task of the interventional radiologist to negotiate the numerous bifurcations in the cardio vessel tree ROI to safely deliver the balloon catheter's tip to the lesioned site. The vessels are connected among each other by shunts and the guidewire must be "threaded" through the appropriate shunts so arrive at the lesion. To provide the radiologist with visual clues about the instant cardio vasculature, a sequence of angiograms (angios) have been previously acquired from the patient either in a previous session by the same imager or by a different imager.

The procedure for acquiring the angios A are basically similar to the procedure described above in connection with the fluoros F however during acquisition of the angios A a high opacity contrast agent ("dye") is delivered to patient Pat and then passes gradually with the blood flow through the vasculature ROI. In other words, the dye or contrast agent furnishes opacity to the otherwise invisible vascular structure ROI and the vascular tree emerges as a spider like footprint in each of the angios A. Because of the dye's progressing through the vasculature, different portions of the vasculature appear in each angiograph in a different intensity or contrast. Contrast or the amount of darkening is therefore different in each angiogram at different positions therein. As mentioned the angiograms are acquired in a preparatory phase prior to above fluoro supported intervention. According to one embodiment, a further preparatory step involves a roadmap extractor RMX operative to extract a series of road map graphics RM from its corresponding angiogram. A device RMX for obtaining said road maps RM from the angios A is explained below with reference to FIG. 4. A road map is a digital mage whose pixel information is indicative to or is capable of showing the outlines of silhouette of the vasculature's footprint as recorded in the corresponding angio.

The whole of the vasculature ROI may be so large that no single angiogram shows each part of said vasculature footprint in equally high contrast or for some reason incomplete angios are recorded. There is normally only a minimal amount of dye injected to avoid adverse health effects in the patient. In other words, as the dye progresses through the vasculature during acquisition of the angiograms, relative to a given position, proximal parts of the vasculature will be sufficiently perfused ("filled") with dye whereas distal parts are not yet sufficiently dye filled or the dye has faded out at the proximal part by the time the distal parts are sufficiently filled.

Broadly speaking, image processor IP operates to receive a stream of the fluoros F and combines each fluoro with a corresponding road map to produce a combined image CI for any received fluoro F. Said combined image CI can then be displayed as a graphics display GD on a monitor M for the benefit of the radiologist during the intervention This is because the so produced graphic display GD will show a guidewire footprint GWF at the position corresponding to the acquisition time of the current fluoro with the corresponding roadmap outlining the contours of the vasculature at the current position of the guide-wire tip. Portions of the vasculature where the tip is not currently resident may not be shown in sufficient contrast however this is not necessary because for the radiologist only the current locality of the guide-wire tip is of interest to safely navigate the guidewire. More specifically, the graphics display GD produced by image processor IP as proposed herein is capable of showing the instant fluoro together with a selected one of a plurality of roadmaps. The roadmap is so selected that the outlines of the vasculature are represented at least with a user adjustable contrast at a user definable vicinity around the current guide-wire tip. According to one embodiment, the contrast is pre-set and cannot be changed by the user.

Image processor IP as proposed herein accounts for the current cardiac phase of the patient when combining the road map with the current fluoro. The cardiac phase is accounted for because cardiac activity impacts the shape and position of the considered vasculature at any given time. The coronary arteries ROI "enmesh" the heart muscle and are periodically displaced as the muscle periodically contracts and dilates during the systolic and diastolic phases, respectively. As a consequence, branches of the vascular tree footprint as recorded by the angios A tend to appear shifted with the diastolic and systolic phases. The image processer IP as proposed herein selects from the available road maps which are held in the data base the one that fits best the current cardiac phase and current position of the guidewire or other interventional device or tool.

Unlike previous solutions, image processor IP operates on a "stock pile" of multiple angiograms that are stored per cardiac phase and selects from same the one that is capable of showing the current guidewire position at least at the user-definable contrast. In other words, the selected contextual angio was not only acquired at a cardiac phase corresponding to the cardiac phase of the current fluoro but was acquired when the dye concentration at the current device position was higher than when the remaining angios for the same cardiac phase were acquired. Because of this high contrast at the relevant local tip position, the roadmap extracted from the contextual angio is "faithful" to the true contours of the vessel at said current device position. This is unlike "one size fits all" approaches of previous systems where there is no plurality road maps to choose from by the system for any given current cardiac phase and a given catheter position. In previous systems a certain roadmap is pre-chosen upfront for any given position and it is that pre-chosen roadmap which is then displayed. Unlike with the image processor IP, in previous system there is no selection during run-time from a plurality of equally synchronized angios with the risk of roadmaps poorly delineating vessels around the current position of an interventional tool at some points during the navigation.

Operation of the image processor IP will now be explained in more detail with reference to FIG. 2.

Operation

Road map or vessel map images RM and their respective angios A are held in a data base DB and are each obtained by extraction from a respective one of a series of angiograms A. As held in database DB, road maps RM and their angios A are grouped into n groups, for example (n=3) groups S1-S3. Each group S1-S3 represents a specific cardiac phase and each road map/angio in the respective group is capable of showing when a footprint of a respective portion of the vasculature at the respective cardiac phase. To follow the cardiac phase in practice, n is in the region of 10<n<18. Because the angios A have been acquired throughout a number of cardiac cycles each cardiac phase group S1-S3 includes a plurality of different road maps per cardiac phase. In other words, each road map in a respective group Si is capable of showing, when displayed, the respective vasculature footprint at substantially the same cardiac phase but each roadmap in said group shows in general a different portion of the vasculature and/or at different contrast or grey pixel values as profusion with contrast dye was different at different times in different vasculature portions. The grouping or classification into the cardiac phases S1-S3 can be implemented for example by an associative array data structure for example "hashes" as known in the PERL programming language. Each roadmap is associated with the respective angio A from which it has been extracted and the cardiac phase grouping of the angios A induces a similar grouping in the set of roadmaps RM extracted or extractable from the grouped angios A.

Processer module IP comprises input port IN, object state determiner SD, device localizer L, road map selector S, and graphics display generator G.

Operation of image processer IP will now be described with reference to a particular fluoro Ft1 but it is understood that a completely analogous operation applies to any fluoroscopic image received at a later time at input port IN.

Upon receipt of fluoro t1, device localizer L detects guide wire footprint GWF in said image. As the shape of the interventional device is in general know, a pattern matching based on grey level thresholding can be applied. In case of guidewire GW, its footprint GWF will in general appear as an elongate structure across the image plain. The tip of the guide wire can be determined following the elongate footprint in tangential direction and registering the image position where a sudden drop in grey level occurs. Said position may then be buffered as the current device position.

Object state detector SD operates based on the received fluoro FT1 to detect the current cardiac phase as recorded therein.

According to one embodiment this is done by retrieving or selecting from the "stock pile" of angios A held in data base DB the one whose vessel footprint shape or curvature as recorded therein fits best to the extracted guidewire footprint GWF and/or other "landmarks" in the angios such as the footprint of another medical device residing in the patent PAT during the intervention. For example, there is frequently a catheter residing in a feeder artery at the entrance to the coronaries through which the dye was administered during the angiography.

According to one embodiment to achieve cardiac phase determination, an alignment or matching operation is carried out between the footprint GWF as extracted from current fluoro Ft1 and parts of the vasculature footprints as recorded in the respective angios A associated with the sought after road map RM for that fluoro Ft1. The Angios A may be held in the same data base DB as the roadmaps RM extracted therefrom or in a different database.

Cardiac phase detector SD comprises as subcomponents a footprint matcher M and a cardiac phase selector CS. Cardiac phase selector CS operates on the output of footprint matcher M as will be now described.

The matching operation of the footprint matcher M rests on the assumption that flexible guide wire GW is residing in a vessel branch of the vasculature and tends therefore to assume the shape of said branch. Each vessel branch in the vasculature ROI changes its spatial configuration as the heart cycles through the different cardiac phases and said spatial configuration change will be imparted on the guide wire GW also. The vasculature ROI including its branches will generally undergo an expansion or contraction with the periodic rise and drop of blood pressure and will also experience a slight to and fro shift in response to said periodic pressure fluctuation. Said shift is also imparted on the guidewire GW residing in the vessel.

Thanks to the dye perfusion in the vasculature during the angiography procedure, a segmenter using grey value thresholding operates on each angio A to obtain respective image portions each representing a vessel tree, that is, the footprint of that part of the vasculature that has been recorded at sufficient contrast in the respective angio A.

According to one embodiment, each vessel tree is then further broken up or segmented into vessel branch footprints. Matcher M then operates to match the shape of the guide wire footprint as obtained in fluoro FT1 to the vessel branch footprints as segmented in the respective angio A.

According to one embodiment, the match is attempted by computing parameters of a transformation that is applied to the guidewire footprint to morph into and/or align said footprint with the shape of the vessel branches footprint in each angio. The parameters define a particular transformation from a pre-set family of transformations. According to one embodiment the parameters describe the entries of a matrix for a rigid or non-rigid affine transformation. According to one embodiment the affine transformation defines a shift across the image plane to superpose the guidewire footprint GWF separately on any of the vessel branch footprints. The transformation defining parameters are then compared and checked and a score for each angio-fluoro match is output. The angio-fluoro score measures the extent to which the transformed guide wire footprint GWF follows the respective vessel branch or branches in the currently considered angio. The best score or a score better than a predefined thresh-hold is then output as a successful match. An identifier for the best match angio or a plurality of best matches angios is then passed on to cardiac phase selector CS. Cardiac phase selector CS then looks up the group of the angio that gave rise to the best score or the score satisfying the thresh-hold thereby establishing the current cardiac phase as recorded by the guidewire footprint GWF's shape and location in the currently considered fluoro Ft1.

According to a preferred embodiment, prior to operation of matcher M there is no sub-segmentation of the segmented vessel tree into vessel sub-branches as described above. Instead, the segmented vessel tree footprint is forwarded to a filter that measures directional contrast along a longitudinal direction of the segmented footprint. This so filtered angio is zeroed outside the segmentation boundary and corresponds to the filter response inside same. A ridge filter can be used to implement this embodiment. A similar filter is then applied to the segmented guidewire footprint GWF. The filtered footprints are then aligned with respect to each other by, for example, shifting the guidewire footprint GWF across the image plane of each angio. For each angio the respective maximum intersection of the guidewire footprint GWF with the respective filtered vessel tree footprint is established. The size in terms of pixels is recorded for each intersection as a score for each fluoro-angio couple. The fluoro-angio couple that yields the largest intersection in the guidewire footprint GWF is considered a match. Similar as above in the previous embodiment, the group of the angio that gave rise to the largest maximal intersection or overlap with the filtered guidewire footprint GWF is looked-up. As mentioned above, more than one angio may be used by matcher M for the matching operation to any one fluoro. Matching would then be carried out for the fluoro in respect of a composite angio including an angio showing the footprint of the dye injecting catheter at the entrance of the coronaries. The composite footprint used for the matching is then formed by the guidewire footprint GW and the footprint of said dye injector catheter. The accuracy of the matching can be enhanced by using this composite approach. Only for the purpose of matching and to establish the cardiac phase, the composite angio is constructed and the above described alignment is carried out with respect to said composite angio.

According to one embodiment, in order to speed up computation time of the above mentioned optimization for the footprint fitting procedure, matcher M is not operating to match in each and every angio but operates only for randomly chosen ones of Angio, each angio representative for one and only one of the groups.

According to another embodiment, the (cardiac phase group) representative angios are not chosen randomly, but according to the response of the vessel tree footprint filter. From each group, the angio that elicits the highest ridge filter response is chosen as the representative angio for said group. In other words, for each cardiac phase, the angio that was acquired when the "global" dye concentration in the vessel was highest is chosen as the representative angio for said group.

Flow control then passes on to road map selector S once cardiac phase selector CS forwarded the identity of said group so determined to road map selector S. Said selector S operates to select from among the angio in said candidate or target group a "contextual" angio that is capable of showing when viewed the vasculature at the determined device tip position at a higher contrast than all or at least than a majority of the angios in said target group. The retrieval or search operation of road map selector S to search for the best or an appropriately contextual roadmap is now confined to the road maps held in the determined group as established by matcher M. It will therefore be appreciated from the above that the cardiac phase determiner SD operates to "usher" the selector S to the right target group and selector then searches only within that group for the contextual angio to so produce the desired contextual roadmap that best fit the current cardio phase and spatial context.

Road map selector S then uses the determined tip position to establish a corresponding position in each of the angios in said determined "target" group. Using pre-defined neighborhood for example a circle, square or ellipse, around said corresponding position in each angio, a corresponding localized contrast score is computed for each angio in said target group.

According to one embodiment, the shift or translation as computed above in one embodiment by matcher M can be used to move the guidewire footprint GWF across each of angio neighborhoods to intersect same and then apply the directional ridge filter to each area of maximal intersection. The filter's response in that intersection area is then taken as a measure for the contrast score. A high response of the ridge filter is taken herein as indicative to the high contrast of the local pixel information. The angiogram used earlier to establish the cardiac phase and to so usher selector S to the instant group may or may not turn out the attract the highest score because said angiogram was scored for global contrast whereas road map selector filters for high contrast in the intersection are only.

An identifier of the highest scoring angio or of one of the angio having a score higher than the majority of angios in said target group is then returned. The vessel roadmap of that contextual angio is then looked-up if already extracted or is extracted upon computing the contextual angio to so produce a contextual roadmap. The contextual angio is "doubly" contextual because it has been determined to fit to both, the current cardiac phase and the current position of the medical device GW. The so determined contextual angio has the highest contrast at said device position or has a contrast higher than a pre-set contrast thresh-hold value. Because of the high contrast at the current tip position, the contextual roadmap extracted therefrom can be taken to outline the true contour of the vessel at the relevant position at high fidelity. As can be appreciated from the above, the operation of image processor IP is two phase because it operates to determine i) current cardiac phase and ii) to determine from a stock pile of candidate angios per determined heart phase the one that visually best fits (that is, has the highest contrast) the vasculature at the current device position. Even though a composite angio comprising footprints of the vessel ROI and dye injection catheter may have been used as described above for the matching operation, no such composite angio is used by roadmap selector S to establish the contextual angio.

The so identified contextual road map is then forwarded to graphics display generator G which operates to overlay the contextual road map onto the current fluoro Ft1 to produce a combined image CIt1. The combined image can be displayed in a graphics display GD on screen M to so assist the interventional radiologist in navigating the vasculature ROI. In the combined image CIt, the pixel information is identical to that of the current fluoro except at pixel positions identified by the roadmap overlaid. The roadmap identified pixel positions, that is, the vessel footprint silhouette is highlighted with respect to the remaining pixel information in the angio to so let the outlines of the vasculature better stand out to the eye of the observer. Highlighting is achieved in one embodiment by color-coding. In one embodiment, the region between the outlining contour is likewise color-coded and the guidewire footprint GWF pixels are coded in different color to achieve a visually high contrast between the two. According to one embodiment, the image portion in the combined image CI inside the contextual roadmap is displayed in red with the guidewire footprint GWF displayed in black.

The above operation of image processor IP are then repeated for any newly received fluoro with acquisition time t>t1. In this manner a sequence of combined images CIt is then produced an output sequentially as graphics displays GDt on screen M, each later combined image updating the earlier one currently displayed.

According to one embodiment the computations of the combined image CIt are repeated for each newly received fluoro Ft or at least are repeated for each newly established cardiac phase, either when computed by cardiac phase detector SD or upon receipt of a signal picked-up by an ECG device. In case of the newly cardiac phase, selector S then refocuses its search in a new group corresponding to the detected cardiac phase and a new roadmap is retrieved and displayed on screen with the new fluoro. The roadmap retrieval and the so retrieved roadmap are therefore kept synchronized with the current cardiac phases.

According to one embodiment, in order to achieve a smooth transition between the consecutively displayed contextual road maps in the respective combined images CIt and to so avoid "flickering", image processor IP's road map selector S includes a temporal smoothing function in the optimization for computing the contextual angio or roadmap in order to avoid sharp "jumps" from one roadmap to a very different one, for instance, from a proximally filled roadmap to a distally filled one in $\frac{1}{15}^{th}$ of a second. According to one embodiment, the smoothing function operates on the ambiguity that results when there is more than one candidate angio whose score is above the threshold, that is, when there are a plurality of contextual or "best" angios. If there are two or more candidate angios Ai, Aj each having respective acquisition times i and j, and if the previous displayed roadmap corresponds to an angio having acquisition time k, roadmap selector S will return angio Ai if |i−k|<|j−k|, and angio Aj otherwise. In other words, in case of score ambiguity, the angio proximate (in time) to the currently displayed one will be returned as contextual angio and the road map associated with said angio will be displayed in the follow up combined image. In this manner a temporal proximity score can be awarded to each angio or its roadmap along with the above mentioned angio-fluoro score. The temporal score imposes a regularization that encourages successive angios to be associated with successive fluoros. Both scores can be consolidated into a composite score and roadmap selector S returns the contextual angio or contextual roadmap RM based on said composite score.

Figure 3:
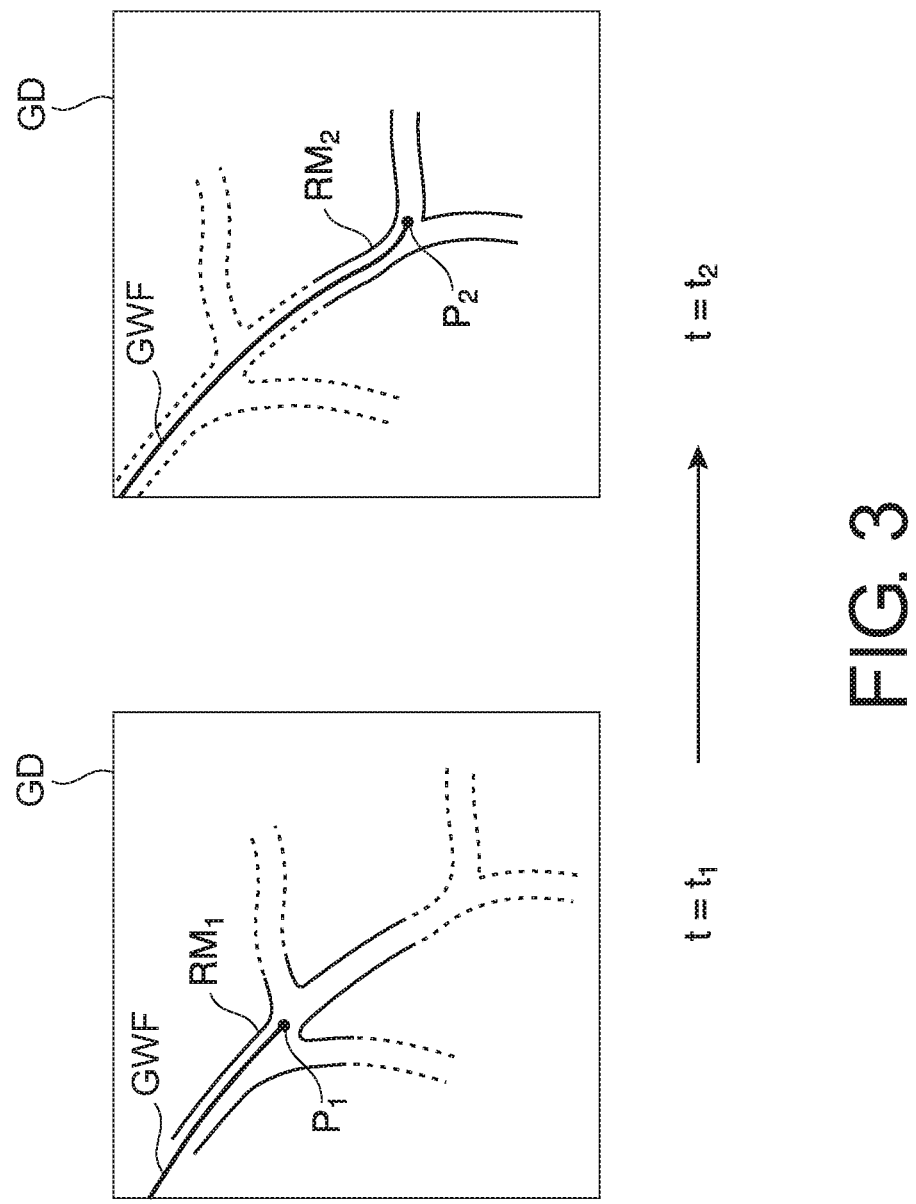
FIG. 3 schematically shows a sequence of graphics displays generated by the image processor of FIG. 2.

With reference to FIG. 3, there is shown a schematic sequence of graphic displays GDt1, GDt2 according to one embodiment as they would appear on screen M at subsequent times t1<t2.

At time t=t1, guidewire GW resides at position P1 as evidenced by guide wire footprint GWF. A proximately focused road map RM1 is displayed which highlights the locale around the current position P1.

As time progresses, at t=t2, graphics display GD is updated because guidewire's position has now changed from P1 to P2. As can be seen the radiologist navigated guide wire through a shunt into a different vessel branch. Previously displayed road map RM1 is no longer displayed and in its stead a, relative to the previous position P1, distally focused, relative road map RM2 is displayed now focused on the newly assumed guidewire position P2. In other words, the sequence of road maps RM1, RM2 are adapted to the current cardiac phase and appear to "follow" the track of the guidewire GW as it progresses through the vasculature. Each roadmap RM1, RM2 results from extraction of the respective contextual angio and each contextual angio is a selection from the respective groups each storing a plurality of equally cardiac phase synchronized angios. As shown in FIG. 3, no stitching together of various road maps is needed for display, only the locally most interesting one of the road maps, that is, the respective contextual one, is displayed at any given time t1, t2. Avoiding displaying a stitched roadmap allows avoiding artifacts that may occur in particular at the transition between the different stitched roadmaps which can mislead the clinician.

Figure 4:
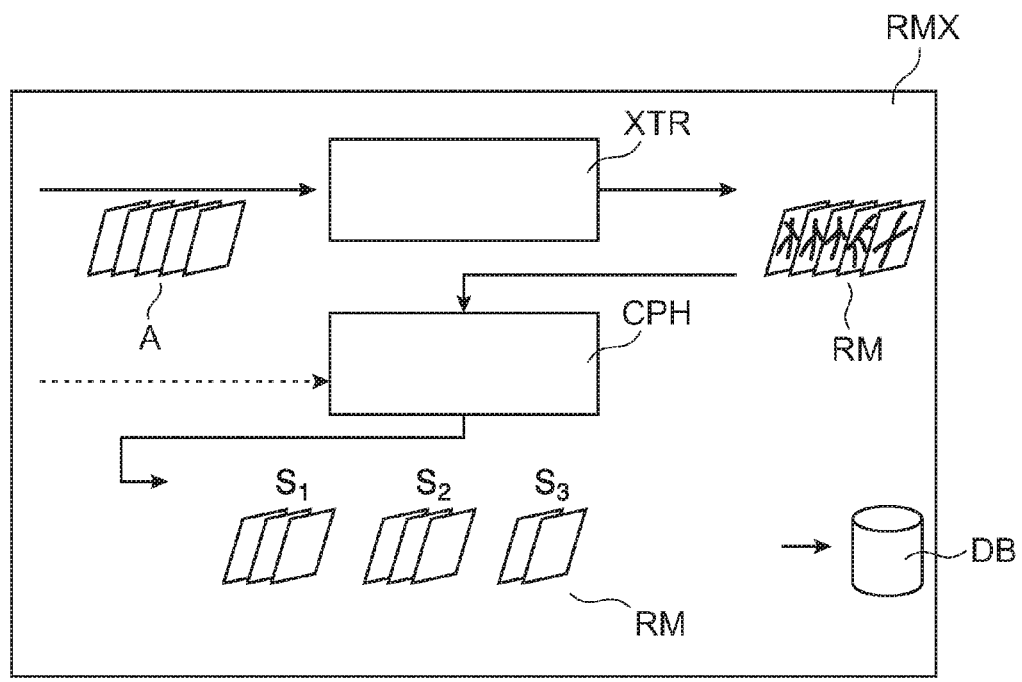
FIG. 4 is a block diagram of components of a device for grouping roadmaps according to states of an imaged object.

With reference to FIG. 4, a road map extractor RMX is shown which can be used to produce the classified or grouped road maps as held in data base DB which image processer IP uses to fashion the series of combined images CI.

According to one embodiment the grouping uses an external ECG signal acquired concurrently with the acquisition of the respective angiogram. Each angiogram is indexed by its respect ECG signal. In that case the grouping is a look up exercise of the respective ECG index to effect the grouping.

According to another embodiment, no external ECG signal is required and the grouping can be achieved by image or pattern recognition among the road maps RM. This can be done because in general the sequence angiograms are acquired over multiple cardiac cycles. Because the thickness and, more pronouncedly, the position of the coronary vessels change periodically, a corresponding similarity will be discernible among the vessel tree footprints. Similar to the operation of footprint matcher M above, each road map is attempted to be brought into alignment with each of the remaining road maps by a suitable transformation and those pair of roadmaps whose alignment achieves the highest score will be considered to belong to the same cardiac phase and will be grouped accordingly.

Extractor XTR receives via a suitable input port (not shown) the stream of angios A. In one embodiment, the ridge filter to detect elongate structures is applied first to each angio. Regions that elicit the highest response are then forwarded to a segmenter. Segmenter then operates on said high filter response portion via grey value thresholding to extract the respective vessel tree footprints as the respective roadmaps RM each associated with their angio from which they have been extracted. The so extracted road maps RM are essentially masked versions of the respective angiograms or filtered angiograms. In other words, pixels that are determined by the segmentation to be part of the vasculature footprint retain their original pixel value whereas remaining pixels are zeroed. In other embodiments, the masking is inverse so pixels inside the vessel footprint are zeroed and pixels outside are preserved The so produced series of road maps is then forwarded to cardiac phase extractor CPH which then produces the grouping of the road maps into cardiac phase groups S1-S2.

As mentioned earlier, operation of road map extractor RMX occurs in a preparatory phase prior to acquisition position of the fluoros during the intervention in other words operation of road map extractor RMX occurs in a phase prior to the operation of image processor IP. However in an alternative embodiment, extraction of roadmaps occurs once the contextual angio has been identified. In this case, no grouping of the roadmaps is carried out and it is only the angios themselves that are grouped into cardiac groups S1-S3.

Figure 2:
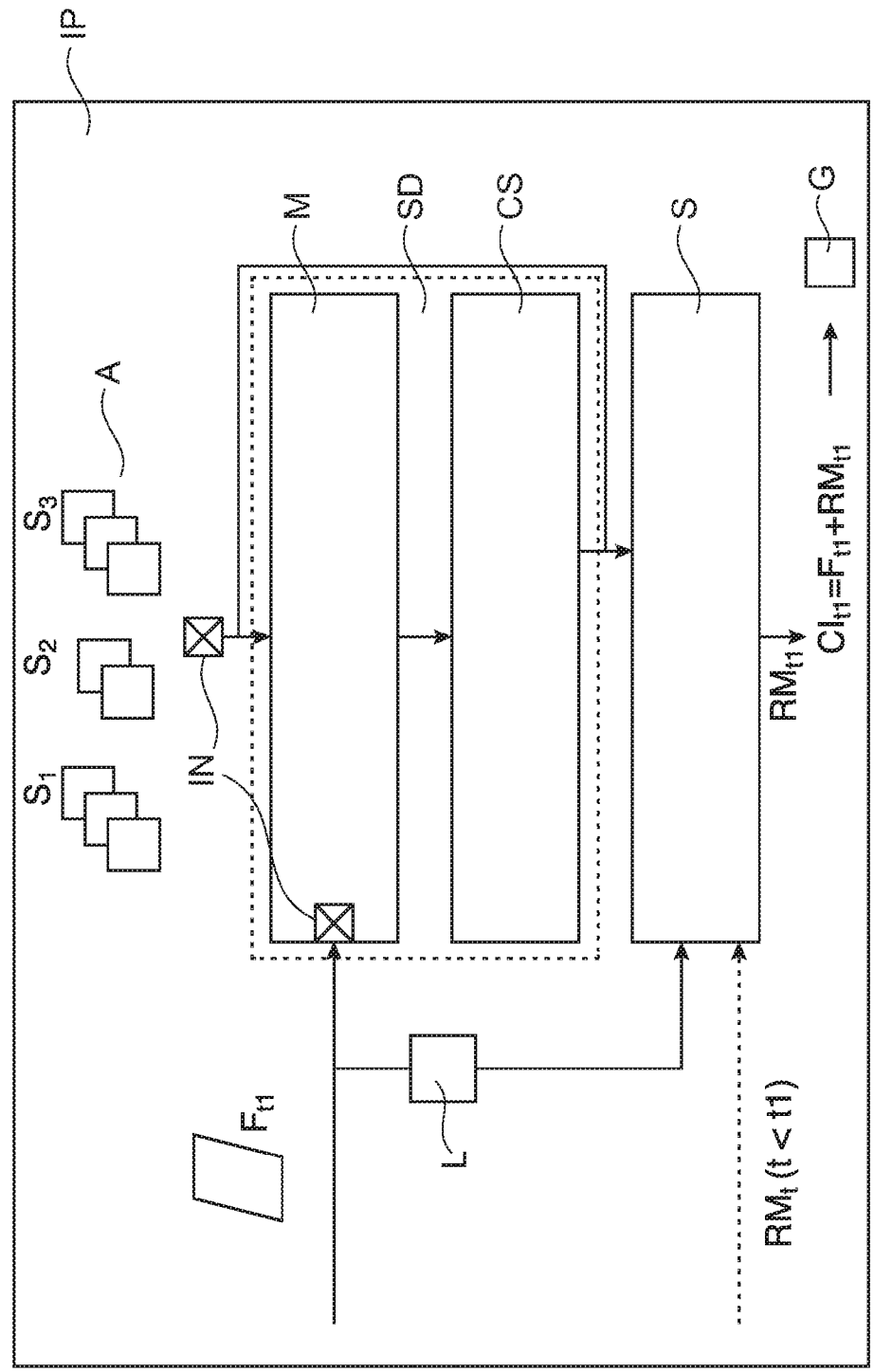
FIG. 2 is a block diagram of components of the image processor of FIG. 1.

Although in FIG. 2 all components or image processor IP are shown to reside on same, this is merely one embodiment. In other embodiments a distributed architecture is used with the components connected in a suitable communication network among each other. Image processor IP can be used as an add-on for existing imagers. According to one embodiment, image processor IP may be arranged as a dedicated FPGA or as hardwired standalone chip or may run as module on console CC. Image processor IP may be programmed in a suitable scientific computing platform such as Matlab® or Simulink® and then translated into C++ or C routines maintained in a library and linked when called on by central operation console CC.

Figure 5:
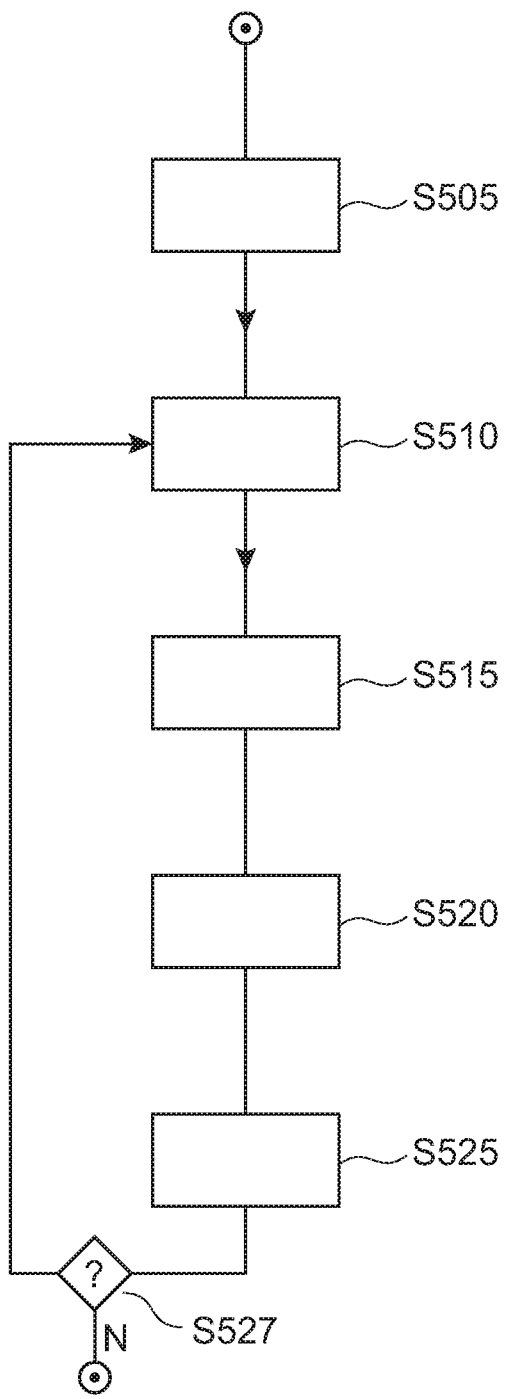
FIG. 5 is a flowchart of an image processing method.

With reference to FIG. 5, a flow chart of an image processing method as proposed herein is shown.

At step S505 the fluoro image acquired at a certain instant is received.

At step 510 a current cardiac phase is determined either based on the received fluoro and sequence of pre-acquired angios or based on externally received ECG signal.

At step S515 a position of the medical device such as the catheter guide wire is determined based on the device's footprint in the received fluoro.

At step S520 a contextual angio is selected from a plurality of stored angios. The angio is selected to fit and correspond to both, the determined cardiac phase and the position as determined earlier in step S510. Selection at S520 is from a plurality of road maps per determined cardiac phase.

In step S525, a contextual roadmap extracted or associated with the selected contextual road is then combined with the current fluoro and the so combined image is then displayed on a screen.

In step S527 it is determined whether a new fluoroscopic image has been received and if yes, the steps S510-S525 are repeated for said newly received fluoro.

The above steps may also be executed in a different order. For example, the steps of detecting the cardiac phase step and the step of determining the device position may occur in the opposite order.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing apparatus comprising
   an input port for receiving a projection image of a device acquired while the device resides at a position relative to an object, the object capable of transitioning between at least a first object state and a second object state, and the device being repositionable;

an object state determiner configured to determine a current state of the object;

a device localizer configured to use image information in the received projection image to determine the position of the device;

an object image selector configured to select a contextual object image from a plurality of stored object images organized in groups corresponding to the first object state and the second object state, respectively, wherein at least one group comprises at least two of the object images, and wherein the selected contextual object image i) is from the group that corresponds to the determined current object state and ii) has image information providing highest contrast indicative of the determined device position within the group; and a graphics display generator configured to generate for display on a screen a combined image including a part of the selected contextual object image and the received device projection image.

2. The apparatus of claim 1, wherein the graphics display generator is configured to generate a new combined image when a new object state is determined by object state determiner.

3. The apparatus of claim 1, wherein, if the group of the contextual object image has the at least two of the object images, the object image selector is configured to use an image neighborhood around the device position in the device image to establish corresponding image neighborhoods in the at least two of the object images in the group of the matched object image, and the object image selector is configured to use a scoring scheme to assign a score to each of the at least two of the object images, the score based on pixel values in the respective established image neighborhoods, wherein the contextual object image is selected as the one of the at least two of the object images that has a higher score than the at least one other of the at least two object images.

4. The apparatus of claim 1, wherein the determination operation of object state determiner includes a matching operation to match the received device image to at least one matching object image among the plurality of stored object images and to return the state corresponding to the matching object image's group as the determined object state.

5. The apparatus of claim 1, wherein the combined image is one where the part is a roadmap image extracted from the object image, the roadmap image overlaid onto the device image.

6. The apparatus of claim 1, wherein the device is a guidewire or other interventional instrument.

7. The apparatus of claim 1, wherein the device images are fluoroscopic images or the object is part of a human or animal vasculature or the object images are angiograms of the object.

8. An image processing system comprising:
an apparatus of claim 1;
an x-ray imager for supplying the device images;
a memory where the plurality of grouped object images are stored; and
the screen.

9. The memory in the system of claim 8.

10. The apparatus of claim 1, wherein the device is a guidewire or other interventional instrument, the device images are fluoroscopic images, the object is part of a human or animal vasculature that transitions between at least the first object state and the second object state, and the object images are angiograms of the human or animal vasculature.

11. An image processing apparatus comprising:
an input port for receiving a projection image of a device acquired while the device resides at a position relative to an object, the object capable of transitioning between at least a first object state and a second object state, and the device being repositionable;

an object state determiner configured to determine a current state of the object;

a device localizer configured to use image information in the received projection image to determine the position of the device;

an object image selector configured to select a from of a plurality of stored object images grouped according to the first object state and the second object state, wherein at least one group comprises more than one of the object images, a contextual object image i) in a group corresponding to the determined object state and ii) having image information indicative of the determined device position; and a graphics display generator configured to generate for display on a screen a combined image including a part of the selected contextual object image and the received device projection image, wherein, if there is a plurality of object images for the device image in the group corresponding to the object state, the object image selector is configured to select the contextual object image as the object image of the plurality of object images having an acquisition time most proximate in time to a previously selected contextual object image.

12. The apparatus of claim 11, wherein the device is a guidewire or other interventional instrument, the device images are fluoroscopic images, the object is part of a human or animal vasculature that transitions between at least the first object state and the second object state, and the object images are angiograms of the human or animal vasculature.

13. An image processing method comprising:
receiving a projection image of a device acquired while the device resides at a position relative to an object, the object capable of transitioning between at least a first object state and a second object state, and the device being repositionable;

determining a current state of the object;

determining the position of the device by using image information in the received projection image;

selecting a contextual object image from a plurality of stored object images organized in groups corresponding to the first object state and the second object state, respectively, wherein at least one group comprises at least two of the object images, and wherein the selected contextual object image i) is from the group that corresponds to the determined current object state and ii) has image information providing highest contrast indicative of the determined device position; and generating for display on a screen a combined image including a part of the selected contextual object image and the received device projection image.

14. The image processing method of claim 13, further comprising:
upon determining a new object state, generating a new combined image based on the newly determined object state.

15. The image processing method of claim 13, wherein, if the group of the contextual object has the at least two of the object images, the selecting includes using an image neighborhood around the device position in the device image to establish corresponding image neighborhoods in the at least two of the object images in the group of the matched object image, and the selecting further includes assigning a score to each of the at least two of the object images, the score based on pixel values in the respective established image neighborhoods; wherein the contextual object image is selected as the one of the at least two of the object images that has a higher score than the at least one other of the at least two object images.

16. A non-transitory computer readable medium having stored thereon a computer program, executable by a processor, for performing the image processing method of claim 13.

17. The method of claim 13, wherein the device is a guidewire or other interventional instrument, the device images are fluoroscopic images, the object is part of a human or animal vasculature that transitions between at least the first object state and the second object state, and the object images are angiograms of the human or animal vasculature.

* * * * *